United States Patent
Nielsen et al.

(10) Patent No.: US 6,432,242 B1
(45) Date of Patent: Aug. 13, 2002

(54) METHOD FOR APPLYING ELASTIC TO A MOVING WEB

(75) Inventors: Jimmy Nielsen, Gothenburg; Peter Berntson, Västra Frölunda; Hakon Lundberg, Sävedalen; Arne Lindqvist, Skövde, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/473,701

(22) Filed: Dec. 29, 1999

(30) Foreign Application Priority Data

Dec. 29, 1998 (SE) ................................................ 9804587

(51) Int. Cl.[7] .............................................. B32B 31/08
(52) U.S. Cl. ...................... 156/164; 156/161; 156/176; 156/177
(58) Field of Search ................................ 156/161, 164, 156/176, 494, 177, 495, 496, 229; 604/385.24, 385.25

(56) References Cited

U.S. PATENT DOCUMENTS

| 4,666,542 A | 5/1987 | De Jonckheere | 156/164 |
| 4,801,345 A | 1/1989 | Dussaud et al. | 156/164 |
| 5,147,487 A | * 9/1992 | Nomura et al. | 156/164 |
| 5,413,654 A | 5/1995 | Igaue et al. | 156/164 |
| 5,500,075 A | 3/1996 | Herrmann | 156/494 |
| 5,531,850 A | 7/1996 | Herrmann | 156/176 |

\* cited by examiner

*Primary Examiner*—Michael W. Ball
*Assistant Examiner*—Todd J. Kilkenny
(74) *Attorney, Agent, or Firm*—Young & Thompson

(57) ABSTRACT

A method for applying elastic, preferably thread elastic, to a travelling web (1) of material in a direction that is generally perpendicular to the feed direction (20) of the web (1). An applicator (9) is moveable generally perpendicular to the web (1) and includes a thread guide (6) which is moveable between two outer positions, the thread guide (6) being adapted to apply elastic (5a–b) to the web (1). The thread guide (6) delivers the elastic (5a–b) to a stopper (16) as it passes the stopper (16) while moving to its outer position and the thread guide (6) again picks up the elastic (5a–b) as it passes the stopper on the way to the other position.

1 Claim, 2 Drawing Sheets

A-A

METHOD FOR APPLYING ELASTIC TO A MOVING WEB

BACKGROUND OF THE INVENTION

The present invention relates to a method and to an arrangement for applying elastic, and then in particular to a method and to an arrangement for applying elastic threads to a travelling web of material, preferably in the manufacture of sanitary articles such as diapers, incontinence protectors, etc.

It is known that sanitary articles, and diapers in particular, comprise an absorbent body, a bottom backing sheet, made of polyethylene for instance, and a top sheet made of nonwoven, for instance. It is often desired in the manufacture of such products to apply elastic threads, elastic ribbons or the like generally transversely to the inner and the outer sheet as seen in the longitudinal direction of a travelling web of material, so as to provide such products with elastic regions, e.g. with leg elastic or waist belts. The products are normally produced continuously on a travelling web with said products moving in the longitudinal direction of the web, hereinafter called the feed direction, wherewith the elastic material, hereinafter called elastic, is applied.

A general problem with applying elastic to travelling webs of material for use in the manufacture of sanitary articles, such as diapers, incontinence protectors, etc., resides in achieving optimal production results, i.e. high production rates and different degrees of stretch in the elastic applied to the web.

Many different elastic applicators are known to the art. Many of these earlier known devices require the travelling web to be stopped, or at least significantly slowed down and then started-up or, in the latter case, accelerated. Other devices allow the web to move continuously, although often at speeds which are so slow as to lower the production rate considerably.

One simple way of applying elastic thread in curved paths on a travelling web is to cause a rotating disc, arranged parallel with the travelling web, to actuate a rod that carries an applicator in the form of a thread guide, said guide being fixed to the disc and caused to move backwards and forwards while applying the elastic thread as the web moves beneath said rod. The elastic thread is applied in a shape similar to that of a "sine curve".

It is sometimes desirable to cut off a part of the curve and make this part straight, i.e. to cut-off the peaks of the "sine curve".

According to one known method, the elastic thread is passed through a channel in a thread guide and then up onto the travelling web. There is placed at the thread guide and the web a stop means, e.g. a stop pin, whose lateral position (perpendicular to the movement direction of the web) determines the size of that part of the curve which is to be cut-off. Since the thread guide is located outwardly of the stop means, the thread passes through both the thread guide and said stop means and therewith result in greater friction, wherewith the force acting on the thread increases. Process-wise, this increases the risk of the thread breaking, particularly when the mean stretch of the thread lies close to a maximum permitted value. It may also be difficult to get the thread to remain on a glued surface, since the thread can readily be "drawn loose". In the manufacture of, e.g., diapers, stretching of the elastic will often be greatest at the front and rear edges of the diaper, and lowest in the crotch region thereof. The opposite is often desired.

It is thus desirable to be able to apply said elastic at a greater speed than has been possible hitherto, and to achieve optimal stretching of the elastic in the finished product. It shall be possible to apply the elastic at a greater speed, without needing to stop or slow down the web.

SUMMARY OF THE INVENTION

One object of the present invention is to provide a method and an arrangement which will enable elastic, preferably elastic thread, to be applied to a travelling web of material at high speed.

Another object of the invention is to provide an arrangement which is particularly suitable for applying elastic to an absorbent garment, such as a diaper, and then preferably curved leg elastic around the leg openings of the diaper.

By elastic is meant in this document all types of elastic threads, elastic ribbons, etc.

According to one preferred embodiment of the invention, there is provided an arrangement for applying elastic, preferably elastic thread, to a travelling web of material in a direction that is generally perpendicular to the web feed direction, said arrangement comprising:

a roller or some corresponding device for feeding the web forwards;

at least one container for storing and/or feeding the elastic to the web;

an applicator for applying the elastic continuously to said web, said applicator and/or a part thereof being moveable along a path which is generally perpendicular to the web feed direction and including a thread guide which is moveable between at least two positions, an inner and an outer position, and which is adapted to apply elastic to said web; and at least one thread stop disposed inwardly of said outer position, wherein the thread guide is constructed to hand the elastic over to the stop as it passes said stop and returns to its outer position, and to pick-up the elastic again as it returns, wherewith the elastic passes through both the thread guide and the stop solely when passing by. This greatly reduces the frictional forces that would otherwise act on the elastic.

The thread guide will conveniently include on one side a recess or notch for accommodating at least one elastic thread, preferably several threads.

The arrangement will also conveniently include slide pins that extend parallel to the plane of the web and which are disposed perpendicular to the web feed direction so as to ensure that the elastic will always have the same vertical position.

The aforedescribed arrangement for applying elastic in accordance with the invention can be used essentially in the manufacture of all types of sanitary articles. The tops of the applied curved elastic can be cut-off on both sides, by providing the arrangement with at least two thread stops, for instance.

The invention also relates to a method of applying elastic, preferably thread elastic, to a travelling web of material, as defined in Claim 1, by feeding the travelling web in one direction and applying elastic to said web with the aid of an applicator that includes a thread guide which moves reciprocatingly between an inner and an outer turning position along a path which extends generally perpendicular to the web feed direction, wherewith the thread guide on said applicator is caused to hand the elastic over to at least one stop means disposed between said turning positions as said thread guide passes the stop means on its way to said outer turning position, whereafter the thread guide picks up the elastic on its way back to said inner turning position. The arrangement will conveniently include one stop means, although several stop means may, of course, be provided.

Thus, when applying the invention, the speed at which the elastic is applied and, in particular controlled stretching of the elastic, is enhanced. A simple and inexpensive manufacturing process is also provided.

The invention will now be described in more detail with reference to preferred embodiments thereof and also with reference to the accompanying drawings.

DETAILED DESCRIPTION OF THE INVENTION

Figure 1A:
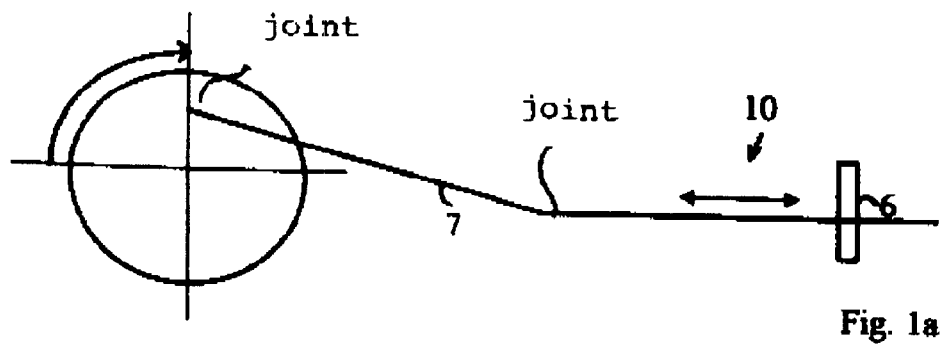
FIG. 1a illustrates how the thread guide that applies the elastic is caused to move forwards and backwards.

FIG. 1a shows how the thread guide 6 that applies the elastic is caused to move forwards and backwards.

Figure 1B:
FIG. 1b is a view from above of an embodiment of an arrangement for applying elastic to a travelling web of material in accordance with the invention.

FIG. 1b illustrates from above one embodiment of an inventive arrangement 10. The illustrated arrangement 10 is particularly usable in applying elastic thread to sanitary articles, such as diapers, etc., although the arrangement is not limited hereto.

Figure 2:
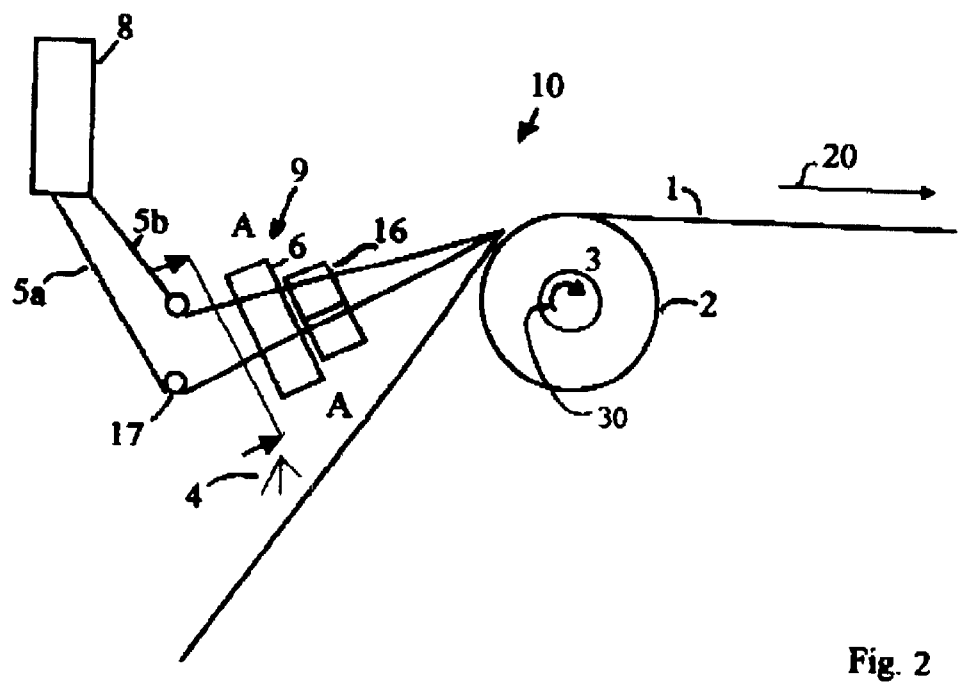
FIG. 2 is a side view of the arrangement illustrated in FIG. 1.

FIG. 2 is a side view of the arrangement 10 shown in FIG. 1b.

The arrangement 10 for applying elastic threads 5a–b includes a device 2 for advancing a web of material 1, said device preferably having the form of a feed roller mounted on a horizontal drive shaft 3. The direction in which the roller rotates is shown by arrow 30 in FIG. 2. The width of the feed roller 2 may vary widely and will depend on the width of the web. The roller 2 will conveniently be slightly wider than the web 1. A spray device 4 (or a heating device) is suitably arranged above the web 4, for spraying glue or some other adhesive substance onto the web 1 on the side thereof that shall receive the elastic thread/threads 5a–b. The spray device 4 is preferably spaced from the feed roller 2 so that glue will not come into contact therewith. The arrangement 10 also includes an elastic thread container 8 arranged upstream of a thread guide 6 and possible slide pins 17.

The elastic threads 5a–b are drawn from the container B and fed in the direction of arrow 20 via the thread guide 6. The elastic threads 5a–b are fed from the container 8 and applied to the travelling web 1. The applied, elastic threads 5a–b will function to render the crotch region or the waist region of a diaper for instance more elastic.

The elastic threads are led through the thread guide 6 and onto the web 1. A number of slide pins 17 are arranged to prevent the threads 5a–b being positioned at wrong heights. The threads 5a–b are guided by the thread guide 6, which causes the threads 5a–b either to be applied in a tensioned state or in a relaxed state. The thread guide 6 is mounted on an arm 7 which is pivotally mounted on, e.g., a frame structure (see FIGS. 1a–b). The pivotal arm 7 can be driven in various different ways, for instance with the aid of an eccentric drive mechanism that includes the arm 7. The arm 7 functions to move the thread guide 6 forwards and backwards in a direction transversal to the web feed direction. The arm 7 can be moved across the full width of the web 1.

Slide pins 17 are conveniently provided to ensure that the threads 5a–b will be located constantly at the same height level.

Figure 3A:
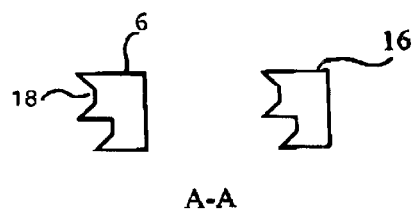
FIG. 3a is an enlarged section view taken on the broken line A—A shown in FIG. 2.

FIG. 3a is a sectional view taken on the line A—A in FIG. 2, showing an appropriate thread guide configuration for receiving the elastic threads 5a–b.

The thread guide 6 suitably includes a recess or notch 18, preferably a flat-bottom U-shaped or V-shaped recess, for receiving the elastic threads 5a–b.

Figure 3B:
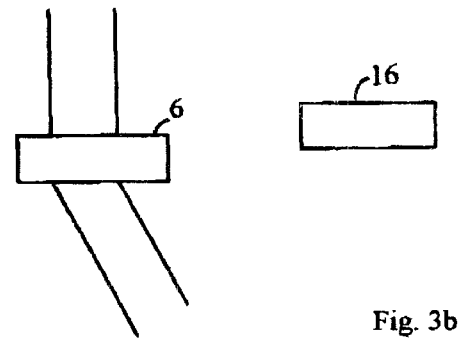
FIG. 3b shows the thread guide in its inner turning position.
Figure 3C:
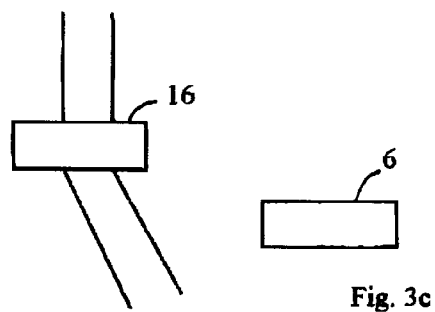
FIG. 3c shows the thread guide in its outer turning position.

As shown in FIGS. 3b–c, the thread guide 6 is constructed so that it will deliver the thread to the stop 16 as it passes said stop while moving to its outer position y. The thread guide 6 is then empty and picks up the thread 5a–b as it returns, such that the thread will pass through both the thread guide 6 and the stop 16. Consequently, the threads 5a–b will only pass through both the thread guide 6 and the stop 16 over a very short period, wherewith only a slight increase or no increase in friction will occur and the threads 5a–b will not therefore be stretched. In actual fact, stretching of the thread or threads in the crotch of the diaper will be somewhat lower by reason of the curve having a straight section due to geometric reasons.

The travelling web 1 may be a plastic film web which in the finished sanitary article will form its backing sheet. Alternatively, the web 1 may consist of a plastic film and nonwoven laminate for instance, or consist of a nonwoven material. In this latter case, the web may form the top sheet material of the finished article, i.e. the liquid-permeable sheet that lies proximal to the wearer in use.

The absorbent bodies and either the top sheet material or the backing sheet material are applied to the web 1 carrying said elastic in a later process stage (not shown), preferably in the longitudinal direction of the web when leg elastic shall be provided. The elastic is thus disposed between the two top sheet and backing sheet webs.

The inventive method/arrangement can also be used to apply waist elastic when so-called cross-production is used, i.e. when the absorbent bodies are placed transversely to the feed direction and are thus not restricted to longitudinal or lengthwise production.

The material from which the backing sheet is made may be polyethylene with a thickness of 0.02–0.04 mm, or some other suitable thermoplastic material. The top sheet may be comprised of polypropylene with a latex binder.

2–3 mm natural rubber threads are an example of the elastic threads used. The elastic threads may be of any kind suitable for the manufacture of said products, such as different types of synthetic rubber, e.g. polyurethane. It is also possible to use combinations of different materials, for instance cotton-spun rubber threads.

The adhesive substance used to fasten the elastic threads to said surface may be hot melt glue.

It is essential that the elastic threads will adhere to said surface with sufficient strength to withstand all other conceivable forms of treatment and other processes carried out in the manufacture of an absorbent article.

Other appropriate application requirements are of a conventional kind and optimum conditions can be readily established by the person skilled in this art, for instance conditions concerning temperature, times, etc.

Although not shown, the sanitary product is cut out after having applied the elastic thread or threads.

In certain product applications with respect to sanitary articles, it is suitable to heat the web material prior to applying the elastic thread or threads. The aforementioned advantages are not affected by this.

Although the invention has been described with reference to preferred embodiments with respect to the application of elastic threads, it will be understood that the invention is not restricted to these embodiments and that all forms of elongated elastic, such as elastic thread, elastic ribbon, etc., lie within the concept of the invention.

It will also be understood that the embodiments described to illustrate the invention can be modified or varied in many different ways, without departing from the scope of the present invention. The scope of the invention is therefore restricted solely by the accompanying Claims.

What is claimed is:

1. A method of applying elastic to a travelling web (1) in a direction generally perpendicular to a feed direction (20) of said web, wherein the method includes the steps of:

feeding the travelling web (1) in the feed direction (20); and applying the elastic (5*a*–*b*) with the aid of an applicator (9) which includes a thread guide (6) that moves reciprocatingly between an inner and an outer turning position generally perpendicular to the web feed direction (20), said thread guide (6) handing over the elastic (5*a*–*b*) to at least one stopper (16) disposed between said turning positions as the thread guide (6) passes said stopper (16) on the way to said outer turning position, said thread guide being empty between said stopper and said outer turning position, whereafter the thread guide (6) takes back the elastic (5*a*–*b*) as said thread guide passes said stopper on the way to said inner turning position, said thread guide carrying the elastic between said stopper and said inner turning position.

* * * * *